United States Patent

Mohrs et al.

Patent Number: 5,126,354
Date of Patent: Jun. 30, 1992

[54] LEUKOTRIENE SYNTHESIS-INHIBITING DISUBSTITUTED (QUINOLIN-2-YL-METHOXY) PHENYLACETIC ACID DERIVATIVES

[75] Inventors: Klaus Mohrs, Wuppertal; Siegfried Raddatz; Romanis Fruchtmann, both of Cologne; Christian Kohlsdorfer, Erftstadt; Reiner Müller-Peddinghaus; Pia Theisen-Popp, both of Bergisch-Gladbach, all of Fed. Rep. of Germany

[73] Assignee: Bayer Aktiengesellschaft, Leverkusen, Fed. Rep. of Germany

[21] Appl. No.: 561,036

[22] Filed: Aug. 1, 1990

[30] Foreign Application Priority Data

Aug. 24, 1989 [DE] Fed. Rep. of Germany ....... 3927931

[51] Int. Cl.$^5$ .................. C07D 215/14; C07D 215/18; C07D 215/20; A61K 31/47
[52] U.S. Cl. .................................... 514/311; 514/312; 546/153; 546/170; 546/174
[58] Field of Search ............... 514/311, 312; 546/153, 546/170, 174

[56] References Cited

U.S. PATENT DOCUMENTS

| | | | |
|---|---|---|---|
| 4,661,499 | 4/1987 | Young et al. | 546/153 |
| 4,929,626 | 5/1990 | Mohrs et al. | 514/311 |

FOREIGN PATENT DOCUMENTS

| | | | |
|---|---|---|---|
| 018156 | 5/1985 | European Pat. Off. | 546/170 |
| 0339416 | 11/1989 | European Pat. Off. | 546/170 |
| 0344519 | 12/1989 | European Pat. Off. | 546/170 |
| 0349062 | 1/1990 | European Pat. Off. | 546/170 |

OTHER PUBLICATIONS

Musser, et al. J. Med. Chem. 1990 33 240–245.
Journal of the Chemical Society Chemical Communications, Jun. 7, 1972, JCCCAR (11) 625–704 (1972).
Chemische Berichte, Gegrundet 1868, G. E. Jeromin, W. Orth, B. Rapp, W. Weiss. Chem. Ber. 120, 649–651 (1987).

Primary Examiner—Robert T. Bond
Assistant Examiner—E. C. Ward
Attorney, Agent, or Firm—Sprung Horn Kramer & Woods

[57] ABSTRACT

Inhibiting leucotriene synthesis in patients with novel disubstituted (quinolin-3-yl-methoxy)phenylacetic acid derivatives of the formula

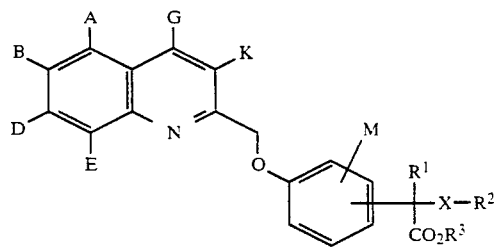

in which
A, B, D, E, G, K and M each independently is H, OH, halogen, $CF_3$, $OCF_3$, COOH, alkyl, alkoxycarbonyl or aryl,
$R^1$ is alkyl or cycloalkyl,
$R^2$ and $R^3$ each independently is H, alkyl or aryl, and
X is O or S,
and salts thereof.

11 Claims, No Drawings

LEUKOTRIENE SYNTHESIS-INHIBITING DISUBSTITUTED (QUINOLIN-2-YL-METHOXY) PHENYLACETIC ACID DERIVATIVES

The invention relates to disubstituted (quinolin-2-yl-methoxy)phenylacetic acid derivatives, processes for their preparation and their use in medicaments.

It is known that 3-(quinolin-2-yl-methoxy)phenylacetic acid and 2-[3-(quinolin-2-yl-methoxy)phenyl]-propionic acid and the methyl and ethyl esters thereof have an anti-inflammatory and antiallergic action (cf. EP-A 181,568).

Disubstituted (quinolin-2-yl-methoxy)phenylacetic acid derivatives of the general formula (I)

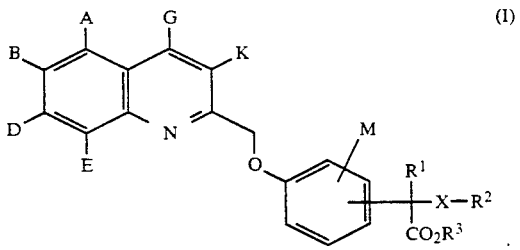

in which
A, B, D, E, G, K and M are identical or different and represent hydrogen, hydroxyl, halogen, trifluoromethyl, trifluoromethoxy or carboxyl,
represent straight-chain or branched alkyl having up to 10 carbon atoms, which is optionally substituted by hydroxyl or halogen,
represent straight-chain or branched alkoxy or alkoxycarbonyl having up to 10 carbon atoms, or
represent aryl having 6 to 10 carbon atoms, which is optionally substituted by halogen, nitro, cyano or by straight-chain or branched alkyl or alkoxy having up to 8 carbon atoms,
$R^1$ represents straight-chain or branched alkyl having up to 10 carbon atoms, which is optionally substituted by halogen or by cycloalkyl having 3 to 8 carbon atoms, or
represents cycloalkyl having 3 to 8 carbon atoms, which is optionally substituted by halogen or straight-chain or branched alkyl having up to 8 carbon atoms,
$R^2$ represents hydrogen or straight-chain or branched alkyl having up to 10 carbon atoms, or represents aryl having 6 to 10 carbon atoms,
$R^3$ represents hydrogen or straight-chain or branched alkyl having up to 10 carbon atoms, or represents aryl having 6 to 10 carbon atoms and
X represents oxygen or sulphur,
and salts thereof, have now been found.

Physiologically acceptable salts are preferred in the context of the present invention. Physiologically acceptable salts of the disubstituted (quinolin-2-yl-methoxy)phenylacetic acid derivatives can be salts of the substances according to the invention with mineral acids, carboxylic acids or sulphonic acids. Particularly preferred salts are, for example, salts with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, propionic acid, lactic acid, tartaric acid, citric acid, fumaric acid, maleic acid or benzoic acid.

Salts in the context of the present invention are moreover salts of monovalent metals, such as alkali metals, and the ammonium salts. Sodium, potassium and ammonium salts are preferred.

Preferred compounds of the general formula (I) are those in which
A, B, D, E, G, K and M are identical or different and represent hydrogen, fluorine, chlorine, trifluoromethoxy or carboxyl,
represent straight-chain or branched alkyl having up to 8 carbon atoms, which is optionally substituted by hydroxyl, fluorine, chlorine or bromine,
represent straight-chain or branched alkoxy or alkoxycarbonyl having up to 8 carbon atoms, or
represent phenyl, which is optionally substituted by fluorine, chlorine, bromine, nitro, cyano or straight-chain or branched alkyl or alkoxy having up to 6 carbon atoms,
$R^1$ represents straight-chain or branched alkyl having up to 8 carbon atoms, which is optionally substituted by fluorine, chlorine, bromine, cyclopropyl, cyclobutyl, cyclopentyl, cyclohexyl or cycloheptyl, or
represents cyclopropyl, cyclobutyl, cyclopentyl, cyclohexyl or cycloheptyl, which is optionally substituted by fluorine, chlorine, or straight-chain or branched alkyl having up to 6 carbon atoms,
$R^2$ represents hydrogen or straight-chain or branched alkyl having up to 8 carbon atoms, or represents phenyl,
$R^3$ represents hydrogen, straight-chain or branched alkyl having up to 8 carbon atoms or phenyl and
X represents oxygen or sulphur,
and salts thereof.

Particularly preferred compounds of the general formula (I) are those in which
A, B, D, E, G, K and M are identical or different and represent hydrogen, fluorine, chlorine, or straight-chain or branched alkyl or alkoxy having up to 6 carbon atoms,
$R^1$ represents straight-chain or branched alkyl having up to 6 carbon atoms, which is optionally substituted by fluorine, cyclopropyl, cyclobutyl, cyclopentyl, cyclohexyl or cycloheptyl, or
represents cyclopropyl, cyclobutyl, cyclopentyl, cyclohexyl or cycloheptyl, which is optionally substituted by fluorine or by straight-chain or branched alkyl having up to 4 carbon atoms,
$R^2$ represents hydrogen, or represents straight-chain or branched alkyl having up to 6 carbon atoms, or represents phenyl,
$R^3$ represents hydrogen, or represents straight-chain or branched alkyl having up to 6 carbon atoms and
X represents oxygen,
and salts thereof.

Especially preferred compounds of the general formula (I) are those in which the quinolylmethoxy grouping on the phenyl is in the 4-position relative to the substituted acetic acid radical.

A process has also been found for the preparation of the compounds of the general formula (I) according to the invention

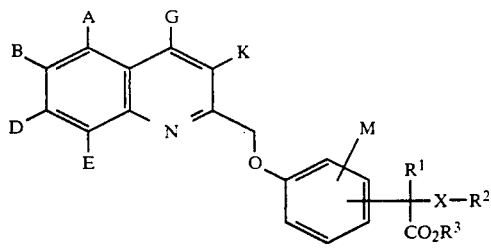

in which A, B, D, E, G, K, M, $R^1$, $R^2$, $R^3$ and X have the abovementioned meanings, which is characterized in that keto esters of the general formula (II)

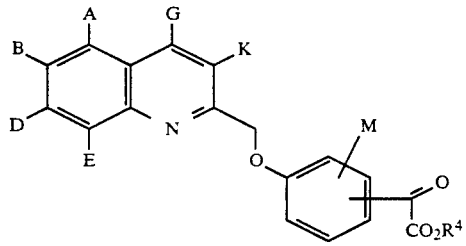

in which

A, B, D, E, G, K and M have the abovementioned meanings, and $R^4$ has the abovementioned meaning of $R^3$ but does not represent hydrogen, are first reduced with Grignard or organometallic compounds of the general formulae (III) and (IIIa)

$R^1$—Y (III)

$(R^1)_n$—Y (IIIa)

in which $R^1$ has the abovementioned meaning, n denotes the number 2 or 3 and

Y represents the typical Grignard radical Z-W, wherein

Z denotes magnesium, cadmium or zinc and

W denotes chlorine, bromine or iodine, or represents lithium, sodium, magnesium, aluminum cadmium or zinc, in inert solvents, and the products are converted, by subsequently splitting off the group Y, into compounds of the general formula (Ia)

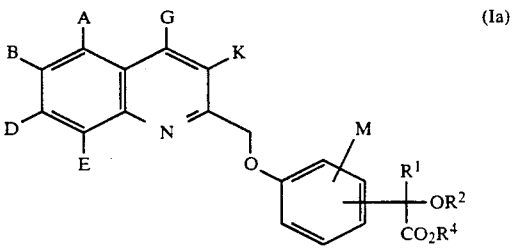

in which A, B, D, E, G, K, M, $R^1$, $R^2$ and $R^4$ have the abovementioned meanings, and in the case where X represents sulphur, the compounds of the formula (Ia) are reacted with thiols of the general formula (IV)

HS—$R^2$ (IV)

in which $R^2$ has the abovementioned meaning, by the customary method, and in the case of the acids the esters are subjected to alkaline hydrolysis in a last step.

The process can be illustrated by the following equation:

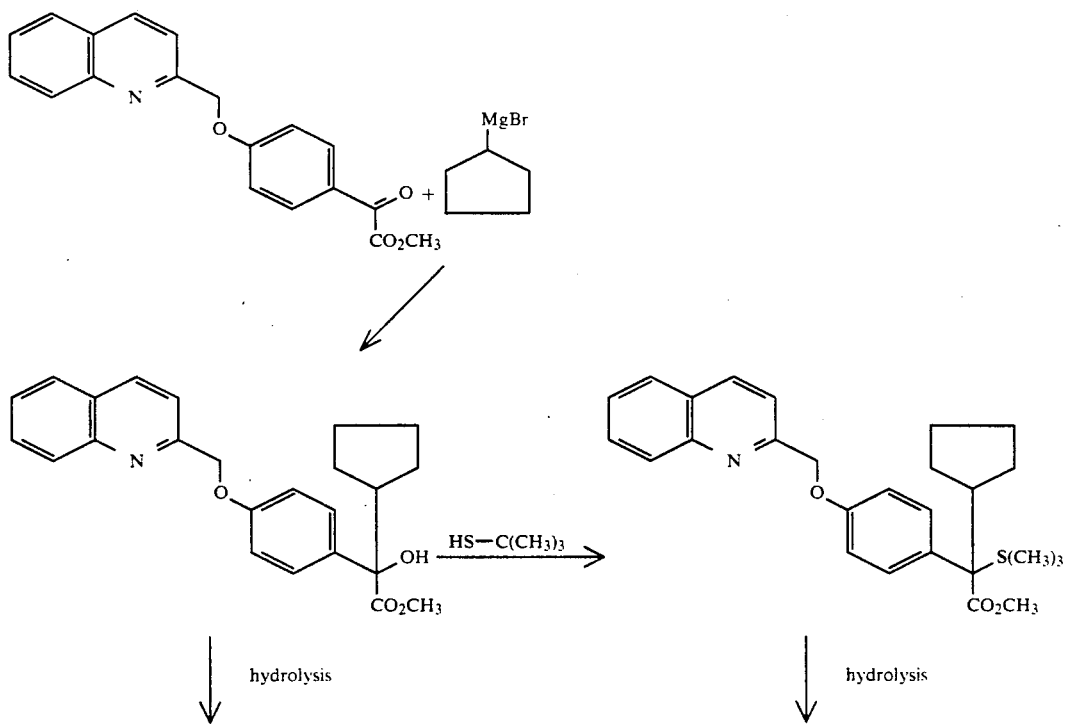

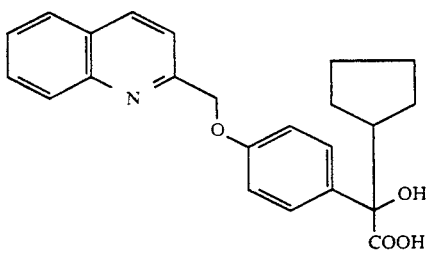
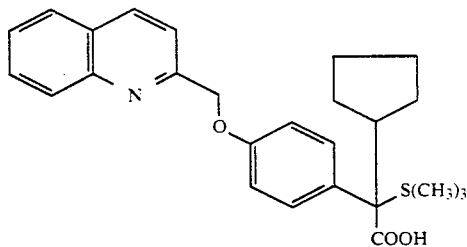

Suitable solvents for the reduction are the customary organic solvents which do not change under the reaction conditions. These include, preferably, ethers, such as diethylether, dioxane, tetrahydrofuran and glycoldimethylether, or hydrocarbons, such as benzene, toluene, xylene, hexane and cyclohexane, or petroleum fractions, or dimethylformamide. It is also possible to use mixtures of the solvents mentioned. Tetrahydrofuran and diethylether are preferred.

The reduction is in general carried out in a temperature range from $-80°$ C. to $+30°$ C., preferably from $-40°$ C. to $+25°$ C.

The reduction is in general carried out under normal pressure. However, it is also possible for the process to be carried out under increased pressure or under reduced pressure (for example in a range from 0.5 to 5 bar).

The group Y is split off by the method customary for Grignard reactions, using aqueous ammonium chloride, solution (cf. J. March, Advanced Organic Chemistry, Second Edition, p. 836).

The compounds of the general formulae (III) and (IIIa) are known per se or can be prepared by customary methods (cf. K. Nützel, Houben-Weyl, Methoden der organischen Chemie [Methods of Organic Chemistry], 4th edition, volume 13/2a, 53 et seq. (Thieme Verlag, Stuttgart) 1973; M. S. Kharash, O. Reinmuth, Grignard Reactions of Nonmetallic Compounds, Prentice Hall, New York, 1974; Uhlman XII, 370; Houben-Weyl XIII/2a, 289–302; R. I. Trust, R. E. Ireland, Org. Synth. 53, 116, (1973); O. Grummitt, E. I. Becker, Org. Synth. Coll. Vol. IV, 771 (1963); H. Adkins, W. Zartman, Org. Synth. Coll. Vol. II, 606 (1943)).

In general, 1 to 3 mols, preferably 1.1 mols, of the Grignard compounds of the organometallic compounds of the general formulae (III) and (IIIa) are employed per mol of reaction partner.

A thiolo or mercapto grouping is introduced in a manner which is known per se (Williamson synthesis) in one of the abovementioned inert solvents and preferably in a phase transfer reaction (cf. Synthesis 447, (1975); J. Am. Chem. Soc. 97, 2345 (1975); J. Am. Chem. Soc. 71, 84 (1949); J. Chem. Soc. 1694 (1962); Synthesis 818 (1974); and Synthesis 430 (1974)).

The thiols of the general formula (IV) are known per se or can be prepared by the customary method (Beilstein 6, 8; 6(3), 1810, 6, 2, 4).

The keto esters of the general formula (II) are new and can be prepared by etherifying compounds of the general formula (V)

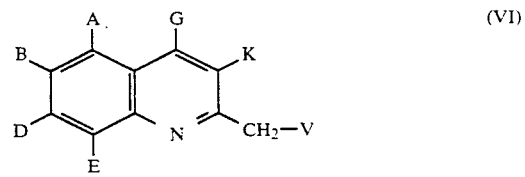

in which
R$^4$ and M have the abovementioned meanings and
T represents a typical hydroxyl-protective group, such as, for example, benzyl or tert.-butyl,
with halogenomethylquinolines of the formula (VI)

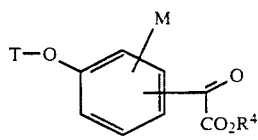

in which
A, B, D, E, G and K have the abovementioned meanings and
V represents halogen,
in inert solvents, if appropriate in the presence of a base, after splitting off the protective group T.

The protective groups are split off from the corresponding ethers by the customary method, for example by hydrogenolytic cleavage of the benzyl ethers in the abovementioned inert solvents in the presence of a catalyst, using hydrogen gas (cf. also Th. Greene: "Protective Groups in Organic Synthesis", J. Wiley & Sons, 1981, New York). "Protective Groups in Organic Synthesis", J. Wiley & Sons, 1981, New York).

The etherification can be carried out in inert organic solvents, if appropriate in the presence of a base.

Solvents for the etherification can be inert organic solvents which do not change under the reaction conditions. These include, preferably, ethers, such as, for example, dioxane, tetrahydrofuran or diethyl ether, halogenohydrocarbons, such as methylene chloride, chloroform, carbontetrachloride, 1,2-dichloroethane or trichloroethylene, hydrocarbons, such as benzene, xylene, toluene, hexane, cyclohexane or petroleum fractions, nitromethane, dimethylformamide, acetonitrile, acetone or hexamethylphosphoric acid triamide. It is also possible to employ mixtures of the solvents.

Bases which can be employed for the etherification are inorganic or organic bases. These include, preferably, alkali metal hydroxides, such as, for example, sodium hydroxide or potassium hydroxide, alkaline earth metal hydroxides, such as, for example, barium hydroxide, alkali metal carbonates, such as sodium carbonate or potassium carbonate, alkaline earth metal carbonates, such as calcium carbonate, or organic amines (trialkyl($C_1$–$C_6$)amines), such as triethylamine, or heterocyclic compounds, such as pyridine, methylpiperidine, piperidine or morpholine.

It is also possible to employ alkali metals, such as sodium, and hydrides thereof, such as sodium hydride, as bases.

The etherification is in general carried out in a temperature range from 0° C. to +150° C., preferably from +10° C. to +100° C.

The etherification is in general carried out under normal pressure. However, it is also possible for the process to be carried out under reduced pressure or increased pressure (for example in a range from 0.5 to 5 bar).

In general, 0.5, to 5, preferably 1 to 2 mols of halide are employed per mol of the reaction partner. The base is in general employed in an amount of 0.5 to 5 mols, preferably 1 to 3 mols, based on the halide.

The compounds of the general formula (V) are known or can be prepared by the customary method (cf. Chem. Commun. 1972, (11), 668).

The compounds of the general formula (VI) are likewise known or can be prepared by the customary method (Chem. Ber. 120, 649 (1987)).

The hydrolysis of the carboxylic acid esters is carried out by customary methods by treating the esters with customary bases in inert solvents.

Suitable bases for the hydrolysis are the customary inorganic bases. These include, preferably, alkali metal hydroxides or alkaline earth metal hydroxides, such as, for example, sodium hydroxide, potassium hydroxide or barium hydroxide, or alkali metal carbonates, such as sodium carbonate or potassium carbonate, or sodium bicarbonate. Sodium hydroxide or potassium hydroxide are particularly preferably employed.

Suitable solvents for the hydrolysis are water or the organic solvents customary for a hydrolysis. These include, preferably, alcohols, such as methanol, ethanol, propanol, isopropanol or butanol, or ethers, such as tetrahydrofuran or dioxane, or dimethylformamide or dimethylsulphoxide. Alcohols, such as methanol, ethanol, propanol or isopropanol, are particularly preferably used. It is likewise possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mols, preferably 1 to 1.5 mols, per mole of the ester employed. Molar amounts of the reactants are particularly preferably used.

Surprisingly, the compounds of the general formula (I) exhibit a high in vitro activity as leucotriene synthesis inhibitors and a potent in vivo action following oral administration.

The disubstituted (quinolin-2-yl-methoxy)phenylacetic acid derivatives according to the invention can be employed as active compounds in medicaments. The substances can act as inhibitors of enzymatic reactions in the context of arachidonic acid metabolism, in particular of 5-lipoxygenase.

They are thus preferably suitable for the treatment and prevention of diseases of the respiratory tract, such as allergies/asthma, bronchitis, emphysema, shock lung, pulmonary hypertension, inflammation/rheumatism and oedemas, thromboses and thromboembolisms, ischaemias (peripheral, cardiac and cerebral disturbances in circulation), cardiac and cerebral infarctions, disturbances in cardiac rhythm, angina pectoris and arterio sclerosis, in cases of tissue transplants, dermatoses, such as psoriasis, inflammatory dermatoses, for example eczema, dermatophyte infection, infections of the skin by bacteria and metastases, and for cytoprotection in the gastrointestinal tract.

The disubstituted (quinolin-2-yl)methoxy)phenylacetic acid derivatives according to the invention can be used both in human medicine and in veterinary medicine.

The pharmacological action data of the substances according to the invention are determined by the following method:

The release of leucotriene $B_4$ ($LTB_4$) on polymorphonuclear rat leucocytes (PMN) after addition of substances and Ca ionophore was determined by means of reverse phase HPLC by the method of Borgeat, P. et al., Proc. Nat. Acad. Sci. 76, 2148–2152 (1979) as a measure of the 5-lipoxygenase inhibition in vitro. The in vivo activity of the compounds was demonstrated with the mouse ear inflammation model in accordance with the method of Young, J. M. et al., J. of Investigative Dermatology 82, 367–371, (1984).

The new active compounds can be converted in a manner known per se into the customary formulations, such as tablets, capsules, coated tablets, pills, granules, aerosols, syrups, emulsions, suspensions and solutions, using inert non-toxic pharmaceutically suitable excipients or solvents. The therapeutically active compound should in each case be present here in the formulation in a concentration of about 0.5 to 90% by weight, preferably 10 to 70% by weight, that is to say in amounts which are sufficient to achieve the stated dosage range.

The formulations are prepared, for example, by extending the active compounds with solvents and/or excipients, if appropriate using emulsifying agents and/or dispersing agents, it being possible, for example in the case where water is used as the diluent, for organic solvents to be used as auxiliary solvents if appropriate.

Examples of auxiliaries which may be mentioned are: water, non-toxic organic solvents, such as paraffins (for example petroleum fractions), vegetable oils (for example groundnut/sesame oil), alcohols (for example ethyl alcohol or glycerol) and glycols (for example propylene glycol and polyethylene glycol), solid excipients, such as natural rock powders (for example kaolins, aluminas, talc or chalk), synthetic rock powders (for example highly disperse silicic acid and silicates) and sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin, sulphite waste liquors, methylcellulose, starch and polyvinylpyrrolidone) and lubricants (for example magnesium stearate, talc, stearic acid and sodium laurylsulphate).

Administration can be performed in the customary manner, preferably orally or parenterally, in particular perlingually or intravenously. In the case of oral use, tablets can of course also contain, in addition to the excipients mentioned, additives, such as sodium citrate, calcium carbonate and dicalcium phosphate, together with various additional substances, such as starch, preferably potato starch, gelatin and the like. Lubricants, such as magnesium stearate, sodium laurylsulphate and talc, can furthermore be co-used for tablet-making. In the case of aqueous suspensions and/or elixirs intended for oral uses, various flavour correctants or dyestuffs can be added to the active compounds, in addition to the above-mentioned auxiliaries.

In the case of parenteral use, solutions of the active compounds can be employed, using suitable liquid excipients.

In general it has proved advantageous in the case of intravenous administration to administer amounts of about 0.01 to 10 mg/kg, preferably about 0.01 to 5 mg/kg of body weight to achieve effective results. In the case of oral administration, the dosage is in general about 0.1 to 200 mg/kg, preferably 1 to 100 mg/kg of body weight.

Nevertheless it may at times be necessary to deviate from the amounts mentioned, and in particular to do so as a function of the body weight or the nature of the administration route, and of the individual behavior towards the medicament, the nature of its formulation and the time or interval at which administration takes place. Thus in some cases it may be sufficient to manage with less than the abovementioned minimum amount, whereas in other cases the upper limit mentioned must be exceeded. Where relatively large amounts are administered, it may be advisable to distribute these into several individual doses over the course of the day.

PREPARATION EXAMPLES

Example I (Formula II)

Methyl 4-(quinolin-2-yl-methoxy)phenylglyoxylate

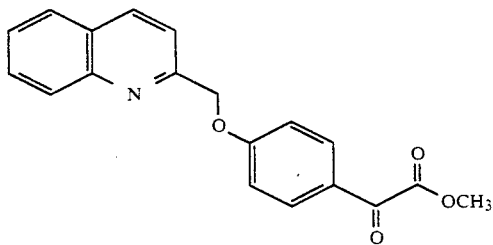

35 g (194 mmol) of methyl 4-hydroxyphenylglyoxylate (Reg. No. 38 250-16-7), 34.5 g (194 mmol) of chloromethylquinoline hydrochloride (Aldrich) and 53.7 g (388 mmol) of potassium carbonate are stirred in 150 ml of dimethylformamide at 50° C. for 20 hours. After cooling to 25° C., 250 ml of water are added and the product is filtered off with suction, dried and recrystallized from methanol.

Yield: 45 g (72% of theory)
Melting point: 105°-108° C. (methanol)

Example 1 (Compounds of the general Formula I)

Methyl 2-[4-(quinolin-2-yl-methoxy)phenyl]-2-cyclopentylhydroxyacetic acid ester

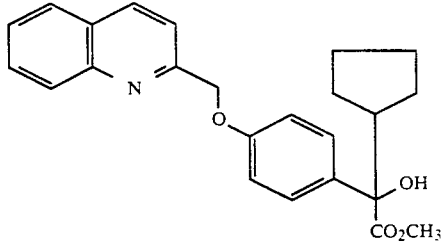

a) Grignard solution 4.9 g (33 mmol) of cyclopentyl bromide are added dropwise to 0.8 g (33 mmol) of magnesium filings in 50 ml of diethyl ether under an inert gas such that the reaction solution boils. The mixture is then heated under reflux for 1 hour.

b) 9.6 g (30 mmol) of methyl 4-(quinolin-2-yl-methoxy)phenylglyoxylacetic acid ester are dissolved in 50 ml of tetrahydrofuran under an inert gas and the solution is cooled to 0° C. The cyclopentylmagnesium bromide solution prepared is added dropwise at 0° C. After heating to 25° C., the reaction mixture is stirred for 15 hours. It is poured onto ice-water, acidified with ammonium chloride and extracted with ethyl acetate. The organic phase is dried with sodium sulphate and evaporated on a rotary evaporator and the crude product is chromatographed on silica gel 60 using cyclohexane/ethylacetate (3:1).

Yield: 3 g (25.5% of theory)
Melting point: 75°-77° C. (ethanol)

Example 2

2-[4-(Quinolin-2-yl-methoxy)phenyl]-2-cyclopentylhydroxyacetic acid

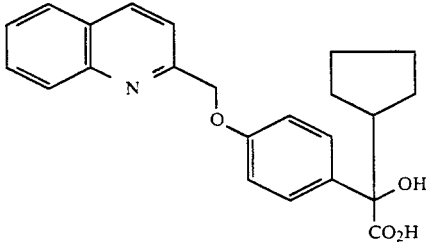

1.1 g (2.8 mmol) of the compound from Example 1 are stirred in 30 ml of methanol and 10 ml of 2 normal sodium hydroxide solution at 25° C. After addition of 10 ml or 2 normal hydrochloric acid, the mixture is concentrated, the residue is taken up in water and the mixture is extracted with ethyl acetate. After drying over sodium sulphate, the mixture is concentrated and the residue is triturated with diisopropyl ether.

Yield: 750 mg (71% of theory)
Melting point: 173°-175° C. (methanol)

Example 3

Methyl 2-[4-(quinolin-2-yl-methoxy)phenyl]-2-cyclohexylhydroxyacetate

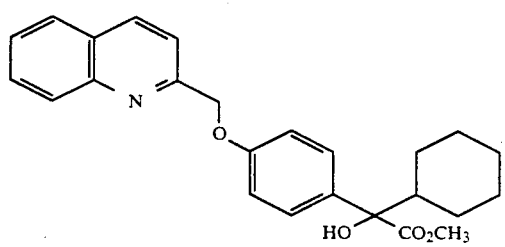

16.1 g (50 mmol) of methyl 4-(quinolin-2-yl-methoxy)phenylglyoxalic acid ester are reacted with 100 mmol of cyclohexylmagnesium bromide as described in Example 1.

Melting point: 126°–128° C. (ethanol)
Yield: 9.6 g (47% of theory)

Example 4

Methyl 2-(4-quinolin-2-yl-methoxy)phenyl]-2-cycloheptylhydroxyacetate

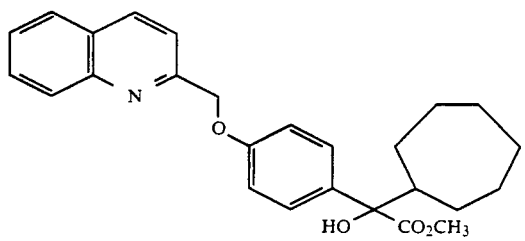

16.1 g (50 mmol) of methyl 4-(quinolin-2-yl-methoxy)phenylglyoxalic acid ester are reacted with 100 mmol of cycloheptylmagnesium bromide as described in Example 1.

Melting point: 102°–103° C. (ethanol)
Yield: 9.7 g (46% of theory)

Example 5

2-[4-Quinolin-2-yl-methoxy)phenyl]-2-cyclohexylhydroxyacetic acid

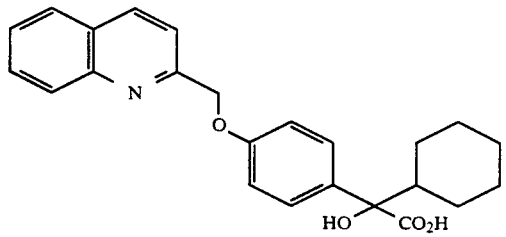

4.05 g (10 mmol) of methyl 2-[4-quinolin-2-yl-methoxy)phenyl]-2-cyclohexyl-hydroxy acetate are hydrolyzed analogously to Example 2.

Melting point: 192°–193° C. (ethanol)
Yield 2.6 g (70% of theory)

Example 6

2-[4-(Quinolin-2-yl-methoxy)phenyl]-2-cycloheptylhydroxyacetate

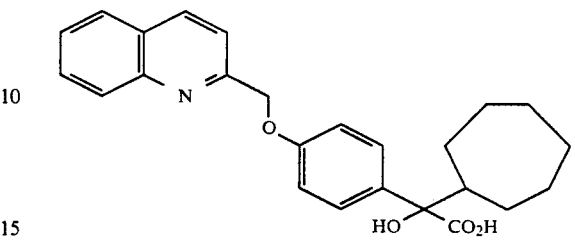

3 g (7.1 mmol) of methyl 2-[4-quinolin-2-yl-methoxy)-phenyl-2-cycloheptyl-hydroxyacetate are hydrolysed analogously to Example 2.

Melting point: 187°–188° C. (ethanol)
Yield: 2 g (69.5% of theory)

It is understood that the specification and examples are illustrative but not limitative of the present invention and that other embodiments within the spirit and scope of the invention will suggest themselves to those skilled in the art.

We claim:

1. A disubstituted (quinolin-2-yl-methoxy) phenylacetic acid derivative of the formula

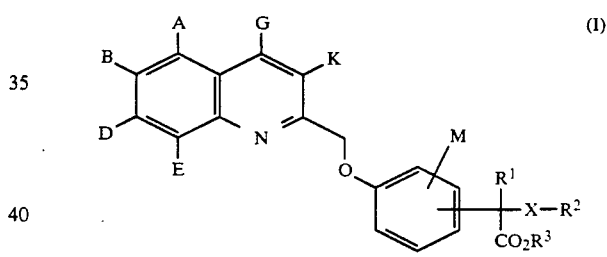

(I)

in which

A, B, D, E, G, K and M are identical or different and represent hydrogen, hydroxyl, halogen, trifluoromethyl, trifluoromethoxy or carboxyl,
represent straight-chain or branched alkyl having up to 10 carbon atoms, which is optionally substituted by hydroxyl or halogen,
represent straight-chain or branched alkoxy or alkoxycarbonyl having up to 10 carbon atoms, or
represent phenyl, which is optionally substituted by halogen, nitro, cyano or by straight-chain or branched alkyl or alkoxy having up to 8 carbon atoms, $R^1$ represents straight-chain or branched alkyl having up to 10 carbon atoms, which is optionally substituted by halogen or by cycloalkyl having 3 to 8 carbon atoms, or
represents cycloalkyl having 3 to 8 carbon atoms, which is optionally substituted by halogen or straight-chain or branched alkyl having up to 8 carbon atoms, $R^2$ represents hydrogen or straight-chain or branched alkyl having up to 10 carbon atoms, or represents phenyl, $R^3$ represents hydrogen or straight-chain or branched alkyl having up to 10 carbon atoms, or represents phenyl and X represents oxygen or sulphur, or a salt thereof.

2. A disubstituted (quinolin-2-yl-methoxy)phenylacetic acid derivative or salt thereof according to claim 1, wherein A, B, D, E, G, K and M are identical or different and represent hydrogen, fluorine, chlorine, trifluoromethoxy or carboxyl, represent straight-chain or branched alkyl having up to 8 carbon atoms, which is optionally substituted by hydroxyl, fluorine, chlorine or bromine, represent straight-chain or branched alkoxy or alkoxycarbonyl having up to 8 carbon atoms, or represent phenyl, which is optionally substituted by fluorine, chlorine, bromine, nitro, cyano or straight-chain or branched alkyl or alkoxy having up to 6 carbon atoms, $R^1$ represents straight-chain or branched alkyl having up to 8 carbon atoms, which is optionally substituted by fluorine, chlorine, bromine, cyclopropyl, cyclobutyl, cyclopentyl, cyclohexyl or cycloheptyl, or represents cyclopropyl, cyclobutyl, cyclopentyl, cyclohexyl or cycloheptyl, which is optionally substituted by fluorine, chlorine, or straight-chain or branched alkyl having up to 6 carbon atoms, $R^2$ represents hydrogen or straight-chain or branched alkyl having up to 8 carbon atoms, or represents phenyl, $R^3$ represents hydrogen, straight-chain or branched alkyl having up to 8 carbon atoms or phenyl and X represents oxygen or sulphur.

3. A disubstituted (quinolin-2-yl-methoxy)phenylacetic acid derivative or salt thereof according to claim 1, wherein A, B, D, E, G, K and M are identical or different and represent hydrogen, fluorine, chlorine, or straight-chain or branched alkyl or alkoxy having up to 6 carbon atoms, represents straight-chain or branched alkyl having up to 6 carbon atoms, which is optionally substituted by fluorine, cyclopropyl, cyclobutyl, cyclopentyl, cyclohexyl or cycloheptyl, or represents cyclopropyl, cyclobutyl, cyclopentyl, cyclohexyl or cycloheptyl, which is optionally substituted by fluorine or by straight-chain or branched alkyl having up to 4 carbon atoms, $R^2$ represents hydrogen, or represents straight-chain or branched alkyl having up to 6 carbon atoms, or represents phenyl, $R^3$ represents hydrogen, or represents straight-chain or branched alkyl having up to 6 carbon atoms and X represents oxygen.

4. A disubstituted (quinolin-2-yl-methoxy)phenylacetic acid derivative or salt thereof according to claim 1, wherein the quinolylmethoxy grouping on the phenyl is in the 4-position relative to the substituted acetic acid radical.

5. A compound according to claim 1, wherein such compound is 2-[4-(quinolin-2-yl-methoxy)phenyl]-2-cyclopentyl-hydroxyacetic acid of the formula

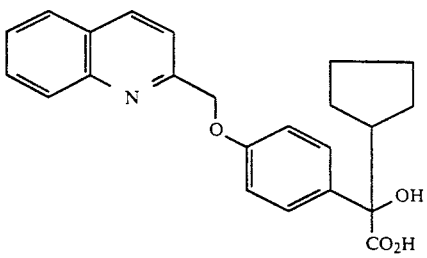

or a salt thereof.

6. A compound according to claim 1, wherein such compound is 2-[4-(quinolin-2-yl-methoxy)phenyl]-2-cyclohexylhydroxyacetic acid of the formula

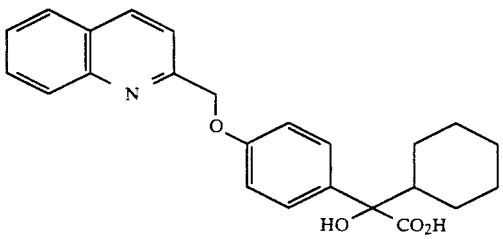

or a salt thereof.

7. A compound according to claim 1, wherein such compound is 2-[4-(quinolin-2-yl-methoxy)phenyl]-2-cycloheptyl-hydroxyacetate of the formula.

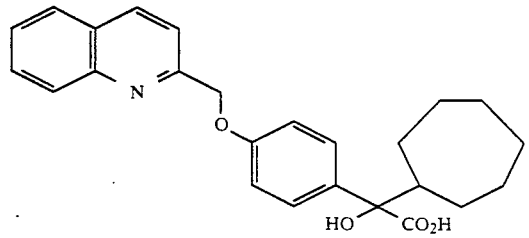

or a salt thereof

8. A leucotriene synthesis-inhibiting composition comprising an amount effective therefor of a compound or salt according to claim 1 and a pharmaceutically acceptable diluent.

9. A method of inhibiting leucotriene synthesis in a patient in need thereof which comprises administering to such patient an amount effective therefor of a compound or salt according to claim 1.

10. The method according to claim 9, wherein such compound is

2-[4-(quinolin-2-yl-methoxy)phenyl]-2-cyclopentyl-hydroxyacetic acid,

2-[4-(quinolin-2-yl-methoxy)phenyl]-2-cyclohexylhydroxyacetic acid or

2-[4-(quinolin-2-yl-methoxy)phenyl]-2-cycloheptyl-hydroxyacetate or a salt thereof.

11. A disubstituted (quinolin-2-yl-methoxy)phenylacetic acid derivative or salt thereof according to claim 1, in which $R^1$ represents cycloalkyl having 3 to 8 carbon atoms, which is optionally substituted by halogen or straight-chain or branched alkyl having up to 8 carbon atoms.

* * * * *

UNITED STATES PATENT AND TRADEMARK OFFICE
CERTIFICATE OF CORRECTION

PATENT NO. : 5,126,354

DATED : June 30, 1992

INVENTOR(S) : Klaus Mohrs, et al.

It is certified that error appears in the above-identified patent and that said Letters Patent is hereby corrected as shown below:

Col. 13, line 46   Before " represents " insert -- $R^1$ --

Signed and Sealed this

Fifteenth Day of March, 1994

Attest:

BRUCE LEHMAN

Attesting Officer    Commissioner of Patents and Trademarks